(12) United States Patent
Lee et al.

(10) Patent No.: US 8,791,072 B2
(45) Date of Patent: Jul. 29, 2014

(54) MODULATING NEUROMUSCULAR JUNCTION DENSITY CHANGES IN BOTULINUM-TOXIN TREATED TISSUE

(75) Inventors: Michael Shi-young Lee, Woodbury, MN (US); Andrew R. Harrison, Minneapolis, MN (US); Linda K. McLoon, Roseville, MN (US)

(73) Assignee: Neuro-Ophthalmix, LLC

( * ) Notice: Subject to any disclaimer, the term of this patent is extended or adjusted under 35 U.S.C. 154(b) by 0 days.

(21) Appl. No.: 13/406,289

(22) Filed: Feb. 27, 2012

(65) Prior Publication Data

US 2012/0220533 A1        Aug. 30, 2012

Related U.S. Application Data

(60) Provisional application No. 61/447,561, filed on Feb. 28, 2011.

(51) Int. Cl.
*A61K 38/00*    (2006.01)
*A61K 38/16*    (2006.01)

(52) U.S. Cl.
USPC .................................... 514/17.7; 514/21.2

(58) Field of Classification Search
None
See application file for complete search history.

(56) References Cited

U.S. PATENT DOCUMENTS

2003/0186853 A1* 10/2003 Wei et al. ........................... 514/9
2005/0196414 A1*  9/2005 Dake et al. ................. 424/239.1

OTHER PUBLICATIONS

Cillino et al. 2009 "Long-term efficacy of botulinum toxin A for treatment of blepharospasm, hemifacial spasm, and apastic entropion: a multicentre study using two drug-dose escalation indexes" Eye 24:600-607.*

De Paiva et al. 1999 "Functional repair of motor endplates after botulinum neurotoxin type A poisoning: Biphasic switch of synaptic activity between nerve sprouts and their parent terminals" PNAS 96:3200-3205.*
Harrison et al. 2006 "Reduction in touch sensitivity and hyperinnervation in vesicant-injured rabbit eyelid by direct injection of corticotropin releasing factor" Neuroscience Letters 400:30-34.*
Fine et al. 2002 "GDNF and NGF released by synthetic guidance channels support sciatic nerve regeneration across a long gap" Eur J Neurosci 15(4):589-601 (abstract only).*
Davidson et al., "The Powerful Cardioprotective Effects of Urocortin and the Corticotropin Releasing Hormone (CRH) Family," Biochemical pharmacology 77, pp. 141-150, 2009.
Harrison et al., "Modulating Neuromuscular Junction Density Changes in Botulinum Toxin-Treated Orbicularis Oculi Muscle", Investigative Ophthalmology & Visual Science, Feb. 2011, vol. 52, No. 2, pp. 982-986.
Alderson et al, "Botulinum-Induced Alteration of Nerve-Muscle Interactions in the Human Orbicularis Oculi Following Treatment for Blepharospasm", Neurology, 1991; 41:1800-1805.
Defazio et al., "Epidemiology of Primary Blepharospasm", Movement Disorders, vol. 17, No. 1, 2002, pp. 7-12.
Holds et al., "Motor Nerve Sprouting in Human Orbicularis Muscle after Botulinum a Injection," Investigative Ophthamology & Visual Science, vol. 31, No. 5, May 1990, pp. 964-967.

* cited by examiner

*Primary Examiner* — Jeffrey Stucker
*Assistant Examiner* — Adam M Weidner
(74) *Attorney, Agent, or Firm* — Schwegman Lundberg Woessner, P.A.

(57) ABSTRACT

A method may include administering botulinum toxin to a tissue of a patient and administering a neuropeptide of the CRF family to the tissue of the patient. In some examples, the botulinum toxin is periodically administered to the tissue of the patient and/or the neuropeptide of the CRF family is periodically administered to the tissue of the patient. The periods with which the botulinum toxin and the neuropeptide of the CRF family are administered may be the same or may be different. In some examples, the botulinum toxin and the neuropeptide of the CRF family are administered to the tissue at substantially the same time, while in other embodiments, the botulinum toxin and the neuropeptide of the CRF family are administered to the tissue at different times.

26 Claims, 9 Drawing Sheets

FIG. 9

MODULATING NEUROMUSCULAR JUNCTION DENSITY CHANGES IN BOTULINUM-TOXIN TREATED TISSUE

This application claims the benefit of U.S. Provisional Application No. 61/447,561, filed Feb. 28, 2011, the content of which is hereby incorporated by reference in its entirety.

TECHNICAL FIELD

The disclosure relates to use of botulinum toxin.

BACKGROUND

Botulinum toxin is a medical treatment for blepharospasm and hemifacial spasm. Developed in the 1970's, injection of botulinum toxin produces a chemodenervation by binding to and paralyzing the neuromuscular junction. Specifically, botulinum toxin may block neurotransmitter release at the neuromuscular junction. The botulinum toxin may specifically cleave SNAP-25, a protein needed for transmitter exocytosis, but may leave the neuromuscular junction intact. Paralyzing the neuromuscular junction paralyzes the surrounding muscle tissue.

Botulinum toxin is an effective, relatively short-term treatment for blepharospasm and hemifacial spasm. Because the treatment is relatively short-term, botulinum toxin must be injected at an average interval of between two and three months for blepharospasm in order to maintain paralysis of the treated muscle. In addition, some patients desire more frequent injections to remain spasm-free and/or due to decreasing sensitivity to the effects of botulinum toxin. Furthermore, some patients develop antibodies to botulinum toxin, requiring increased dosing to achieve similar levels of paralysis or rendering the patient substantially unresponsive to treatment.

The return of muscle function after botulinum toxin injection is believed to be caused by sprouting of axonal collaterals from presynaptic nerve endings at neuromuscular junctions of botulinum toxin-affected muscles. Nerve sprouting after botulinum toxin treatment results in a significant increase in new acetylcholine receptors on the treated muscle compared to muscle that has not been treated with botulinum toxin. These newly formed acetylcholine receptors are in locations distinct from those of the original, paralyzed neuromuscular junctions.

In some cases, peripheral nerve sprouting in the area affected by the botulinum toxin can be measured as early as 3 days after injection of the botulinum toxin. Compound action potentials demonstrate the return of 20% of normal neuromuscular junction activity in patients as early as 7 days after botulinum toxin injection. This rapid and early sprouting of neuromuscular junctions may result in some muscle function returning to the area affected by the botulinum toxin as early as the sixth day. Quantification of neuromuscular junction numbers in rabbit extraocular muscle at various times after botulinum toxin injection has shown doubling of neuromuscular junctions in the treated area within the first month after botulinum toxin treatment. This is one of the major limitations of botulinum toxin use in patients with focal dystonias; the duration of effectiveness is too short to allow permanent alteration of muscle innervation and muscle force.

SUMMARY

Techniques and compositions that may increase the effective duration of botulinum toxin against blepharospasm, hemifacial spasm, and focal dystonias by utilizing a molecule in the corticotropin releasing factor (CRF) family in conjunction with the botulinum toxin are described herein. The CRF family is a group of related neuropeptides in vertebrates. The CRF family is currently understood to consist of CRF (also referred to as corticotropin-releasing hormone (CRH)), urocortin, urotensin-I, and sauvagine. CRF family neuropeptides may reduce or substantially prevent increase in the density of neuromuscular junctions near the location of the CRF family neuropeptide introduction, which may reduce or substantially prevent return of muscle function after botulinum toxin-induced muscle paralysis.

Increasing the duration of effectiveness of botulinum toxin may reduce the need for or frequency of repeat botulinum toxin injections. Additionally, increasing the duration of effectiveness of botulinum toxin may reduce the lifetime exposure of a patient to the drug, which may reduce the likelihood of the patient exhibiting decreased sensitivity to the treatment. More efficacious botulinum toxin therapy is beneficial because there are few other widely accepted choices for medical management of blepharospasm and hemifacial spasm, and none that rival botulinum toxin in clinical efficacy.

In one aspect, the disclosure is directed to a method that includes administering botulinum toxin to a tissue of a patient and administering a neuropeptide of the CRF family to the tissue of the patient.

In another aspect, the disclosure is directed to a kit that includes botulinum toxin and a neuropeptide of the CRF family.

In an additional aspect, the disclosure is directed to a composition that includes botulinum toxin and a neuropeptide of the CRF family.

The details of one or more examples are set forth in the accompanying drawings and the description below. Other features, objects, and advantages of the disclosure will be apparent from the description and drawings, and from the claims.

BRIEF DESCRIPTION OF THE DRAWINGS

FIG. 9 is a bar diagram that illustrates quantification of neuromuscular junction density of various samples of orbicularis oculi muscles.

DETAILED DESCRIPTION

Figure 1A:
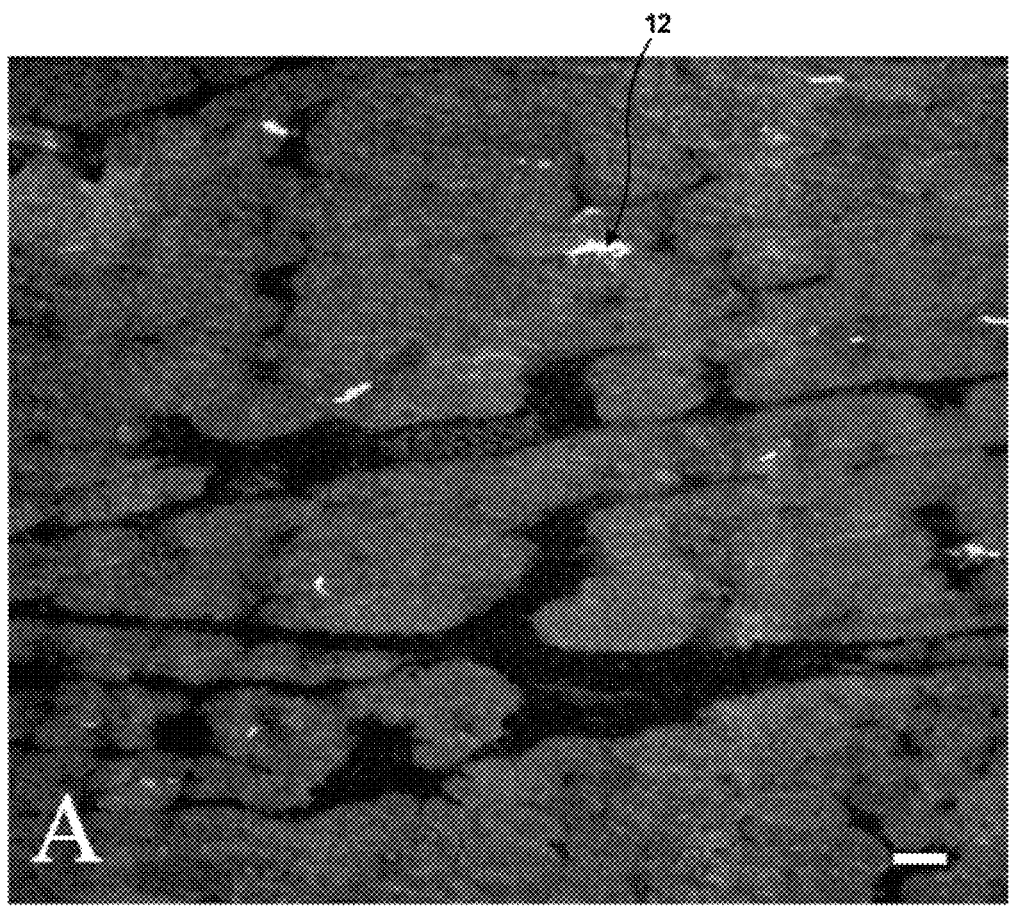
FIGS. 1A-1C are photomicrographs of neuromuscular junctions stained with fluorescently labeled α-bungarotoxin.

Techniques and compositions for improving the duration of effect of botulinum toxin to selectively weaken a single or small group of skeletal muscles are described herein. In accordance with aspects of this disclosure, test agents that have the potential to enhance the duration of paralysis due to botulinum toxin treatment have been investigated. Agents that enhance the duration of paralysis due to botulinum toxin potentially may decrease the number of injections of botulinum toxin needed by a patient over the course of time. Agents investigated in this disclosure for use in conjunction with botulinum toxin include neuropeptides from the CRF family, antibody to insulin growth factor (anti-IGF), and antibody to insulin growth factor-I receptor (anti-IGFIR).

The CRF family is a group of related neuropeptides in vertebrates. The CRF family is currently understood to consist of CRF (also referred to as CRH), urocortin, urotensin-I, and sauvagine. Further details regarding the CRF family may be found in, for example, S. M. Davidson, A. E. Rybka, and P. A. Townsend, *The Powerful Cardioprotective Effects of Urocortin and the Corticotropin Releasing Hormone (CRH) Family*, 77 Biochem. Pharmacol. 141-150 (2009), which is incorporated herein by reference in its entirety.

The CRF family neuropeptides have potent anti-inflammatory effects when applied locally in tissues for treatment of pain. When injected into an inflamed eyelid, CRF family neuropeptides can significantly reduce inflammatory cell infiltrate and nerve fibers at the site of injection. In accordance with aspects of this disclosure, CRF family neuropeptides may reduce or substantially prevent increase in the density of neuromuscular junctions near the location of the CRF family neuropeptide introduction, which may reduce or substantially prevent return of muscle function after botulinum toxin-induced muscle paralysis.

Insulin growth factor (IGF) is a neurotrophic and muscle growth factor that increases in muscles after nerve injury. Co-injection of inhibitory binding proteins specific for IGF, such as IGF binding protein-4, may reduce botulinum-induced sprouting in the levator ani muscle. Local injection of antibodies to soluble neurotrophic factors and their receptors, such as IGF and IGF receptor (IGFR), may reduce collateral axonal branching after nerve injury. Antibodies to IGF (anti-IGF) and antibodies to IGFR (anti-IGFR) have inhibitory effects on IGF effects in tissue. Using either anti-IGF or anti-IGFR has the potential to effectively reduce the botulinum toxin-induced nerve sprouting and corresponding increase in neuromuscular junction density locally within treated orbicularis oculi muscle.

Described herein is a method in which neuropeptides from the CRF family or anti-IGFR are injected into muscle tissue such as, for example, the eyelid muscles. Injection of neuropeptides from the CRF family or anti-IGFR may reduce axonal sprouting and the neuromuscular junction formation that occurs after botulinum toxin injection. In some examples, reduced axonal sprouting and neuromuscular junction formation may increase of the duration of effect of botulinum toxin treatment, thereby reducing the need for repeat injections and thus reducing the overall lifetime exposure to the drug in patients with chronic focal dystonias.

As described above, botulinum toxin directly binds to the neuromuscular junction and prevents neurotransmitter release. The botulinum toxin specifically cleaves SNAP-25, a protein needed for transmitter exocytosis, but leaves the neuromuscular junction intact. This botulinum toxin-induced paralysis leads to sprouting of the terminal nerves that project to the poisoned neuromuscular junctions. These sprouts induce the formation of new neuromuscular junctions, and these new motor endplates are responsible for return of muscle function at the onset of recovery. Eventually, over the course of about 1 month to about 3 months, there is a return of function at the original motor endplates, and the sprouts are eliminated. Inhibition of nerve sprouting at the muscle level should extend the duration of effectiveness of botulinum toxin treatment.

Use of neuropeptides of the CRF family, such as CRF, as an anti-sprouting treatment is a result of its potent analgesic effects with respect to peripheral nerves within injured tissue. Localized injection of CRF has been shown to decrease PGP 9.5-positive nerve density in inflamed eyelid tissue. This reduction in nerve fiber density correlates with a reduction in tissue hypersensitivity to touch.

As described herein, neuropeptides from the CRF family can prevent the formation of new motor endplates in tissue previously treated with botulinum toxin. Neuropeptides from the CRF family also can act directly by reducing synaptic transmission. Reducing synaptic transmission could also potentially alter muscle contractile properties. As CRF is a United States of America Food and Drug Administration (FDA)-approved medication, local injection of neuropeptides from the CRF family, such as CRF, is a particularly attractive approach for extending the duration of botulinum toxin's paralyzing effects in the treatment of blepharospasm and related focal dystonias.

Muscle paresis and paralysis induce the expression of a number of neurotrophic molecules that play a role in peripheral nerve regeneration. Insulin growth factor-I (IGFI) and insulin growth factor-II (IGFII) are particularly potent in increasing the rate of peripheral nerve regeneration, with IGFI playing a role in initial sprouting and subsequent elongation of the regenerating axons. IGFI levels may significantly increase as early as 3 days after a single injection of botulinum toxin and remain elevated for up to one month. As increased levels of IGFI can increase terminal sprouting, decreasing or inactivating IGFI-related molecules may reduce terminal sprouting. Local treatment at the site of paralyzed muscles with either IGF-binding protein-4 or -5 may result in suppression of terminal sprouting. Antibodies to IGFI (anti-IGFI), when focally applied, can result in reduction of terminal axon branching of injured facial nerve.

Injection of anti-IGF or anti-IGFIR after treatment of a tissue with botulinum toxin may reduce or prevent new neuromuscular junction formation caused by botulinum toxin locally within the paralyzed orbicularis oculi muscle.

While the following examples are primarily directed to injection of botulinum toxin and one of a neuropeptide of the CRF family or anti-IGFIR into eyelids of rabbits, botulinum toxin and at least one of neuropeptides from the CRF family, anti-IGF, or anti-IGFIR are expected to provide similar results in human patients.

Botulinum toxin may be used to treat a variety of neuromuscular disorders in patients. For example, botulinum toxin may be used in treatment of dystonias, such as blepharospasm, hemifacial spasm, or focal dystonias. Examples of focal dystonias include torticollis and muscle spasticity secondary to cerebral palsy or other neuromuscular disorders. Botulinum toxin may also be used to treat neuropathic pain and chronic migraines. Botulinum toxin has also been used in cosmetic procedures, such as facial treatments or to treat hyperhidrosis, for example, on the underarms or palms of a patient. Neuropeptides from the CRF family, anti-IGF, and/or anti-IGFIR may be utilized to extend the effective duration of botulinum toxin in any of these uses.

As used herein botulinum toxin may include any form of botulinum toxin, including botulinum toxin A and/or botulinum toxin B. One example of botulinum toxin A is available under the trademark BOTOX® (botulinum toxin), from Allergan, Inc., Irvine, Calif. Botulinum toxin A is also available in other forms and from other companies.

In some examples, botulinum toxin may be provided to a clinician or other user in powder form, and the clinician or other user may mix the botulinum toxin powder in a solvent to form a solution of botulinum toxin in the solvent. For example, the clinician or other user may mix the botulinum toxin in saline to form a solution. Solvents other than saline also may be used to form the botulinum toxin solution. In some examples, the botulinum toxin may be provided to the clinician or other user as a solution, for example, in a vial or in a syringe. In other examples, the botulinum toxin may be provided in other forms, such as, for example, a topical lotion or cream for application on a patient's skin, or as a coating on a topical patch that the patient or clinician applies on the skin of the patient.

In some examples, the at least one of a neuropeptide of the CRF family, anti-IGF, or anti-IGFR may be supplied to the clinician or other user separate from the botulinum toxin. Similar to the botulinum toxin, the neuropeptide of the CRF family, anti-IGF, or anti-IGFIR may be provided in one or more of a variety of forms, such as a powder, a mixture or suspension, a topical location or cream, or a patch.

In some examples, at least one of a neuropeptide of the CRF family, anti-IGF, or anti-IGFIR may be administered to the patient separate from the botulinum toxin. For example, botulinum toxin and the at least one of a neuropeptide of the CRF family, anti-IGF, or anti-IGFIR may be injected into approximately the same tissue via two, separate injections. The at least one of a neuropeptide of the CRF family, anti-IGF, or anti-IGFIR may be administered to the patient before, or after, or at approximately the same time as the botulinum toxin is administered to the patient.

In other examples, the botulinum toxin and at least one of a neuropeptide of the CRF family, anti-IGF, or anti-IGFIR may be administered to the patient in a single step. In some such examples, the botulinum toxin and at least one of a neuropeptide of the CRF family, anti-IGF, or anti-IGFIR are provided to the clinician or other user separate from each other, and the clinician or other user prepares a mixture or solution that includes both the botulinum toxin and the at least one of a neuropeptide of the CRF family, anti-IGF, or anti-IGFIR. For example, the botulinum toxin and the at least one of a neuropeptide of the CRF family, anti-IGF, or anti-IGFIR may be mixed in a single solution and administered together to the patient using a syringe (e.g., in a single injection).

In other examples, the botulinum toxin and the at least one of a neuropeptide of the CRF family, anti-IGF, or anti-IGFIR may be provided to the clinician or other user already combined. For example, the botulinum toxin and the at least one of a neuropeptide of the CRF family, anti-IGF, or anti-IGFIR may be mixed in a single solution and provided to the clinician or other user as the single solution. As another example, botulinum toxin and at least one of a neuropeptide of the CRF family, anti-IGF, or anti-IGFIR may be mixed in a topical lotion or cream, or in a coating on a topical patch.

In some examples, the clinician or other user may administer the botulinum toxin and the at least one of a neuropeptide of the CRF family, anti-IGF, or anti-IGFIR to the patient a single time. In other examples, the clinician or other user may administer the botulinum toxin and the at least one of a neuropeptide of the CRF family, anti-IGF, or anti-IGFIR to the patient at irregular intervals. In other examples, the clinician or other user may administer the botulinum toxin and the at least one of a neuropeptide of the CRF family, anti-IGF, or anti-IGFIR to the patient periodically based on the effective duration of the botulinum toxin and/or the at least one of a neuropeptide of the CRF family, anti-IGF, or anti-IGFIR, in order to substantially maintain the desired therapeutic effect on the patient.

In some examples, the botulinum toxin and the at least one of a neuropeptide of the CRF family, anti-IGF, or anti-IGFIR may be administered periodically on substantially the same schedule. In such examples, the botulinum toxin and the at least one of a neuropeptide of the CRF family, anti-IGF, or anti-IGFIR may be administered to the patient at substantially the same time each time the botulinum toxin and the at least one of a neuropeptide of the CRF family, anti-IGF, or anti-IGFIR are administered to the patient. For example, the botulinum toxin and the at least one of a neuropeptide of the CRF family, anti-IGF, or anti-IGFIR may be administered to the patient during the same office visit. As described above, in some examples, the botulinum toxin and the at least one of a neuropeptide of the CRF family, anti-IGF, or anti-IGFIR may be administered to the patient in a common administration, e.g., in an injection of a solution that includes both the botulinum toxin and the at least one of a neuropeptide of the CRF family, anti-IGF, or anti-IGFIR. In other examples, the botulinum toxin and the at least one of a neuropeptide of the CRF family, anti-IGF, or anti-IGFIR may be administered to the patient in separate administrations, e.g., separate injections of the botulinum toxin and the at least one of a neuropeptide of the CRF family, anti-IGF, or anti-IGFIR.

In other examples, the botulinum toxin and the at least one of a neuropeptide of the CRF family, anti-IGF, or anti-IGFIR may be administered to the patient periodically or at irregular intervals, and the clinician or other user may administer the botulinum toxin and the at least one of a neuropeptide of the CRF family, anti-IGF, or anti-IGFIR to the patient on different schedules. For example, the clinician may administer the botulinum toxin more frequently or less frequently than the clinician administers at least one of a neuropeptide of the CRF family, anti-IGF, or anti-IGFIR to the patient.

In general, when the clinician or other user administers the botulinum toxin to the patient more than one time, the clinician may administer the botulinum toxin to the patient as often as every 8 weeks. The maximum time period between botulinum toxin administration is not limited, but in some examples may be less than about 1 year. In some examples, the time period between a first botulinum toxin administration and a second, subsequent botulinum toxin administration may be about 6 months, about 3 months, between about 3 months and about 6 months, between about 3 months and about 4 months, between about 8 weeks and about 24 weeks, or about 8 weeks. The preceding time periods are merely examples, and a clinician or other user may administer a subsequent botulinum toxin therapy to the patient at any time after a previous botulinum toxin therapy.

For each botulinum toxin therapy, the clinician or other user may administer between about 5 Units and about 300 Units of botulinum toxin. In some examples, the clinician or other user may administer substantially the same dosage of botulinum toxin to the patient for each administration of the botulinum toxin. In other examples, the clinician or other user may administer a different dosage of botulinum toxin for at least one administration of botulinum toxin than a dosage of botulinum toxin for at least one other administration of botulinum toxin.

For example, if a patient has not previously received botulinum toxin treatment for blepharospasm, a first dose of botulinum toxin (e.g., botulinum toxin A) may be between about 2.5 and about 5.0 Units of botulinum toxin per injection site. In some examples, each eyelid may receive be injected at about 5 injection sites, for a total dose of about 12.5 to about 25 units of botulinum toxin per eyelid. In some examples, total dose may be less than about 75 Units of botulinum toxin per eyelid (e.g., less than about 15 Units of botulinum toxin per injection). In some examples, the ranges of botulinum toxin dosage may apply to botulinum toxin A, and dosage ranges of botulinum toxin B may be between about 20 and about 25 times the dosage ranges of botulinum toxin A.

As described above, the clinician or other user may administer at least one of a neuropeptide of the CRF family, anti-IGF, or anti-IGFIR at the same time as the botulinum toxin, at a different time than the botulinum toxin, on the same schedule as the botulinum toxin, and/or on a different schedule than the botulinum toxin. Regardless of the relationship between the administration of the botulinum toxin and the at least one of a neuropeptide of the CRF family, anti-IGF, or anti-IGFIR, the time between a first administration of at least one of a neuropeptide of the CRF family, anti-IGF, or anti-IGFIR and a second, subsequent administration of at least one of a neuropeptide of the CRF family, anti-IGF, or anti-IGFIR may be about 6 months, about 3 months, between about 3 months and about 6 months, between about 3 months and about 4 months, between about 8 weeks and about 24 weeks, or about 8 weeks. The preceding time periods are merely examples, and a clinician or other user may administer a subsequent administration of at least one of a neuropeptide of the CRF family, anti-IGF, or anti-IGFIR to the patient at any time after a previous administration of at least one of a neuropeptide of the CRF family, anti-IGF, or anti-IGFIR.

For each administration of at least one of a neuropeptide of the CRF family, anti-IGF, or anti-IGFIR, the clinician or other user may administer between about 20 micrograms (µg) and about 200 µg of at least one of a neuropeptide of the CRF family, anti-IGF, or anti-IGFIR, such as between about 75 µg and about 200 µg, or between about 150 µg and about 160 µg, or about 150 µg, or about 160 µg for the CRF family neuropeptide, and between about 20 µg and about 50 µg for anti-IGF and anti-IGFIR. In some examples, the clinician or other user may administer substantially the same dosage of at least one of a neuropeptide of the CRF family, anti-IGF, or anti-IGFIR to the patient for each administration of the at least one of a neuropeptide of the CRF family, anti-IGF, or anti-IGFIR. In other examples, the clinician or other user may administer a different dosage of at least one of a neuropeptide of the CRF family, anti-IGF, or anti-IGFIR for at least one administration of at least one of a neuropeptide of the CRF family, anti-IGF, or anti-IGFIR that a dosage of at least one of a neuropeptide of the CRF family, anti-IGF, or anti-IGFIR for at least one other administration of at least one of a neuropeptide of the CRF family, anti-IGF, or anti-IGFIR. The above ranges of at least one of a neuropeptide of the CRF family, anti-IGF, or anti-IGFIR is merely examples, and other amounts of at least one of a neuropeptide of the CRF family, anti-IGF, or anti-IGFIR may be administered to the patient.

In one aspect, the disclosure describes a method including administering botulinum toxin to a tissue of a patient; and administering a neuropeptide of the CRF family to the tissue of the patient.

In some examples, the neuropeptide of the CRF family consists of a neuropeptide selected from the group consisting of CRF, urocortin, urotensin-I, sauvagine, and combinations thereof.

In some examples, the neuropeptide comprises CRF.

In some examples, administering the neuropeptide of the CRF family to the tissue of the patient includes administering CRF to the tissue of the patient at substantially the same time as administering botulinum toxin to a tissue of a patient.

In some examples, administering botulinum toxin to the tissue of the patient and administering the neuropeptide of the CRF family to the tissue of the patient comprise injecting a solution including botulinum toxin and the neuropeptide of the CRF family into the tissue of the patient.

In some examples, administering botulinum toxin to the tissue of the patient and administering the neuropeptide of the CRF family to the tissue of the patient include applying a topical lotion including botulinum toxin and the neuropeptide of the CRF family onto a tissue of the patient.

In some examples, administering botulinum toxin to the tissue of the patient and administering the neuropeptide of the CRF family to the tissue of the patient include applying a patch including a coating including botulinum toxin and the neuropeptide of the CRF family onto a tissue of the patient.

In some examples, administering botulinum toxin to the tissue of the patient includes administering botulinum toxin to the tissue of the patient at a first time, and administering the neuropeptide of the CRF family to the tissue of the patient includes administering the neuropeptide of the CRF family to the tissue of the patient at a second time different than the first time.

In some examples, administering the neuropeptide of the CRF family to the tissue of the patient comprises injecting a solution including the neuropeptide of the CRF family into the tissue of the patient.

In some examples, administering the neuropeptide of the CRF family to the tissue of the patient includes applying a topical location including the neuropeptide of the CRF family to the tissue of the patient.

In some examples, administering the neuropeptide of the CRF family to the tissue of the patient comprises applying a topical patch including a coating including the neuropeptide of the CRF family to the tissue of the patient.

In some examples, administering botulinum toxin to the tissue of the patient comprises injecting a solution including botulinum toxin into the tissue of the patient.

In some examples, administering botulinum toxin to the tissue of the patient comprises applying a topical lotion including botulinum toxin into the tissue of the patient.

In some examples, administering botulinum toxin to the tissue of the patient comprises applying a topical patch including a coating including botulinum toxin into the tissue of the patient.

In some examples, administering botulinum toxin to the tissue of the patient comprises administering botulinum toxin to the tissue of the patient a first time, and the method further comprises administering botulinum toxin to the tissue of the patient a second time.

In some examples, a time between administering botulinum toxin to the tissue of the patient the first time and administering botulinum toxin to the tissue of the patient the second time is greater than about 8 weeks.

In some examples, a time between administering botulinum toxin to the tissue of the patient the first time and administering botulinum toxin to the tissue of the patient the second time is less than about 1 year.

In some examples, a time between administering botulinum toxin to the tissue of the patient the first time and administering botulinum toxin to the tissue of the patient the second time is about 6 months.

In some examples, a time between administering botulinum toxin to the tissue of the patient the first time and administering botulinum toxin to the tissue of the patient the second time is about 3 months.

In some examples, a time between administering botulinum toxin to the tissue of the patient the first time and administering botulinum toxin to the tissue of the patient the second time is between about 3 months and about 6 months.

In some examples, a time between administering botulinum toxin to the tissue of the patient the first time and administering botulinum toxin to the tissue of the patient the second time is between about 3 months and about 4 months.

a time between administering botulinum toxin to the tissue of the patient the first time and administering botulinum toxin to the tissue of the patient the second time is between about 8 weeks and about 24 weeks.

In some examples, administering the neuropeptide of the CRF family to the tissue of the patient comprises administering the neuropeptide of the CRF family to the tissue of the patient a first time, and the method further comprises administering the neuropeptide of the CRF family to the tissue of the patient a second time.

In some examples, a time between administering the neuropeptide of the CRF family to the tissue of the patient the first time and administering the neuropeptide of the CRF family to the tissue of the patient the second time is greater than about 8 weeks.

In some examples, a time between administering the neuropeptide of the CRF family to the tissue of the patient the first time and administering the neuropeptide of the CRF family to the tissue of the patient the second time is less than about 1 year.

In some examples, a time between administering the neuropeptide of the CRF family to the tissue of the patient the first time and administering the neuropeptide of the CRF family to the tissue of the patient the second time is about 6 months.

In some examples, a time between administering the neuropeptide of the CRF family to the tissue of the patient the first time and administering the neuropeptide of the CRF family to the tissue of the patient the second time is about 3 months.

In some examples, a time between administering the neuropeptide of the CRF family to the tissue of the patient the first time and administering the neuropeptide of the CRF family to the tissue of the patient the second time is between about 3 months and about 6 months.

In some examples, a time between administering the neuropeptide of the CRF family to the tissue of the patient the first time and administering the neuropeptide of the CRF family to the tissue of the patient the second time is between about 3 months and about 4 months.

In some examples, a time between administering the neuropeptide of the CRF family to the tissue of the patient the first time and administering the neuropeptide of the CRF family to the tissue of the patient the second time is between about 8 weeks and about 24 weeks.

In some examples, administering botulinum toxin to the tissue of the patient comprises administering botulinum toxin to the tissue of the patient a first time, administering the neuropeptide of the CRF family to the tissue of the patient comprises administering the neuropeptide of the CRF family to the tissue of the patient a first time, and the method further includes administering botulinum toxin to the tissue of the patient a second time, and administering the neuropeptide of the CRF family to the tissue of the patient a second time.

In some examples, a first time between administering botulinum toxin to the tissue of the patient the first time and administering botulinum toxin to the tissue of the patient the second time is substantially the same as a second time between administering the neuropeptide of the CRF family to the tissue of the patient the first time and administering the neuropeptide of the CRF family to the tissue of the patient the second time.

In some examples, a first time between administering botulinum toxin to the tissue of the patient the first time and administering botulinum toxin to the tissue of the patient the second time is different than a second time between administering the neuropeptide of the CRF family to the tissue of the patient the first time and administering the neuropeptide of the CRF family to the tissue of the patient the second time.

In some examples, the first time is greater than the second time.

In some examples, the first time is less than the second time.

In some examples, administering botulinum toxin to the tissue of the patient comprises periodically administering botulinum toxin to the tissue of the patient, and administering the neuropeptide of the CRF family to the tissue of the patient comprises periodically administering the neuropeptide of the CRF family to the tissue of the patient.

In some examples, periodically administering botulinum toxin to the tissue of the patient comprises periodically administering botulinum toxin to the tissue of the patient according to a first schedule, and periodically administering the neuropeptide of the CRF family to the tissue of the patient comprises periodically administering the neuropeptide of the CRF family to the tissue of the patient according to a second schedule.

In some examples, the first schedule is the same as the second schedule.

In some examples, the first schedule is different than the second schedule.

In some examples, periodically administering botulinum toxin to the tissue of the patient comprises periodically administering botulinum toxin to the tissue of the patient with a period of at least about 8 weeks.

In some examples, periodically administering botulinum toxin to the tissue of the patient comprises periodically administering botulinum toxin to the tissue of the patient with a period of between about 3 months and about 6 months.

In some examples, periodically administering the neuropeptide of the CRF family to the tissue of the patient comprises periodically administering the neuropeptide of the CRF family to the tissue of the patient with a period of at least about 8 weeks.

In some examples, periodically administering the neuropeptide of the CRF family to the tissue of the patient comprises periodically administering the neuropeptide of the CRF family to the tissue of the patient with a period of between about 3 months and about 6 months.

In some examples, administering botulinum toxin to the tissue of the patient comprises administering between about 5 Units and about 300 Units of botulinum toxin to the tissue of the patient.

In some examples, administering the neuropeptide of the CRF family to the tissue of the patient comprise administering between about 75 µg and about 200 µg of the neuropeptide of the CRF family to the tissue of the patient.

In some examples, administering the neuropeptide of the CRF family to the tissue of the patient comprise administering about 160 µg of the neuropeptide of the CRF family to the tissue of the patient.

In some examples, administering the neuropeptide of the CRF family to the tissue of the patient comprise administering about 160 µg of the neuropeptide of the CRF family to the tissue of the patient and administering botulinum toxin to a tissue of a patient comprises administering about 5 Units of botulinum toxin to the tissue of the patient.

In another aspect, the disclosure describes a kit including a first container, a second container, botulinum toxin disposed in the first container, and a neuropeptide of the CRF family disposed in the second container.

In some examples, the neuropeptide of the CRF family comprises a neuropeptide selected from the group consisting of CRF, urocortin, urotensin-I, sauvagine, and combinations thereof In some examples, the neuropeptide of the CRF family comprises CRF.

In some examples, the botulinum toxin comprises botulinum toxin A.

In some examples, the botulinum toxin comprises botulinum toxin in powder form.

In some examples, the kit further includes a solvent disposed in the first container, wherein the botulinum toxin is mixed in the solvent.

In some examples, the first container and the second container comprise the same container, a solvent is disposed in the container, and the botulinum toxin and the neuropeptide of the CRF family are mixed in the solvent.

In some examples, the kit further includes a solvent disposed in the second container, and the neuropeptide of the CRF family is mixed in the solvent.

In some examples, at least one of the first container or the second container includes a syringe.

In some examples, the kit includes a first solvent in the first container and a second solvent in the second container.

In some examples, the botulinum toxin is mixed in the first solvent and the neuropeptide of the CRF family is mixed in the second solvent.

In some examples, the first container includes a first syringe, and the second container includes a second syringe.

In some examples, the kit further includes a lotion in a container.

In some examples, the lotion includes the botulinum toxin.

In some examples, the lotion includes the neuropeptide of the CRF family.

In some examples, the lotion includes the botulinum toxin and the neuropeptide of the CRF family.

In some examples, the kit further includes a topical patch including a coating.

In some examples, the coating includes the botulinum toxin.

In some examples, the coating includes the neuropeptide of the CRF family.

In some examples, the coating includes the botulinum toxin and the neuropeptide of the CRF family.

In another aspect, the disclosure describes a composition comprising botulinum toxin and a neuropeptide of the CRF family.

In some examples, the neuropeptide of the CRF family comprises a neuropeptide selected from the group consisting of CRF, urocortin, urotensin-I, sauvagine, and combinations thereof.

In some examples, the neuropeptide of the CRF family comprises CRF.

In some examples, the botulinum toxin comprises between about 5 Units and about 300 Units of botulinum toxin.

In some examples, the neuropeptide of the CRF family comprises between about 75 µg and about 200 µg of the neuropeptide of the CRF family.

In some examples, the neuropeptide of the CRF family comprises about 160 µg of the neuropeptide of the CRF family.

In some examples, the neuropeptide of the CRF family comprises about 160 µg of the neuropeptide of the CRF family and the botulinum toxin includes about 5 Units botulinum toxin.

In some examples, the composition further includes a solvent.

In some examples, the neuropeptide of the CRF family comprises at least one of CRF, urocortin, urotensin-I, or sauvagine.

In some examples, the neuropeptide of the CRF family comprises CRF.

In another aspect, the disclosure is directed to a method including mixing botulinum toxin and a neuropeptide of the CRF family in a carrier to form a composition comprising botulinum toxin and the neuropeptide of the CRF family.

In some examples, mixing botulinum toxin and the neuropeptide of the CRF family in the carrier comprises mixing botulinum toxin and a neuropeptide selected from the group consisting of CRF, urocortin, urotensin-I, sauvagine, and combinations thereof in the carrier.

In some examples, the neuropeptide selected from the group consisting of CRF, urocortin, urotensin-I, sauvagine, and combinations thereof comprises CRF.

In some examples, mixing botulinum toxin and the neuropeptide of the CRF family in the carrier comprises mixing botulinum toxin and the neuropeptide of the CRF family in the carrier in a solvent.

In some examples, mixing botulinum toxin and the neuropeptide of the CRF family in the solvent comprises mixing botulinum toxin and the neuropeptide of the CRF family in the carrier in saline.

In some examples, mixing botulinum toxin and the neuropeptide of the CRF family in the carrier comprises mixing between about 5 Units and about 300 Units botulinum toxin and between about 75 µg and about 200 µg of the neuropeptide of the CRF family in the carrier.

In some examples, mixing between about 5 Units and about 300 Units botulinum toxin and between about 75 µg and about 200 µg of the neuropeptide of the CRF family in the carrier comprises mixing between about 5 Units and about 300 Units botulinum toxin and between about 125 µg and about 175 µg of the neuropeptide of the CRF family in the carrier.

In some examples, mixing botulinum toxin and the neuropeptide of the CRF family in the carrier comprises mixing botulinum toxin and the neuropeptide of the CRF family in a carrier to form a topical lotion comprising botulinum toxin and the neuropeptide of the CRF family.

In some examples, mixing botulinum toxin and the neuropeptide of the CRF family in the carrier comprises mixing botulinum toxin and the neuropeptide of the CRF family in a carrier to form a coating of a topical patch comprising botulinum toxin and the neuropeptide of the CRF family.

In another aspect, the disclosure describes a method including periodically administering botulinum toxin to a tissue of a patient and periodically administering a neuropeptide of the CRF family to the tissue of the patient.

In some examples, periodically administering botulinum toxin to the tissue of the patient comprises periodically administering botulinum toxin to the tissue of the patient according to a first schedule, and periodically administering the neuropeptide of the CRF family to the tissue of the patient comprises periodically administering the neuropeptide of the CRF family to the tissue of the patient according to a second schedule.

In some examples, the first schedule is the same as the second schedule.

In some examples, the first schedule is different than the second schedule.

In some examples, periodically administering botulinum toxin to the tissue of the patient comprises periodically administering botulinum toxin to the tissue of the patient with a period of at least about 8 weeks.

In some examples, periodically administering botulinum toxin to the tissue of the patient comprises periodically administering botulinum toxin to the tissue of the patient with a period of less than about 8 weeks.

In some examples, periodically administering botulinum toxin to the tissue of the patient comprises periodically administering botulinum toxin to the tissue of the patient with a period of about 6 months.

In some examples, periodically administering botulinum toxin to the tissue of the patient comprises periodically administering botulinum toxin to the tissue of the patient with a period of about 3 months.

In some examples, periodically administering botulinum toxin to the tissue of the patient comprises periodically administering botulinum toxin to the tissue of the patient with a period of between about 3 months and about 6 months.

In some examples, periodically administering botulinum toxin to the tissue of the patient comprises periodically administering botulinum toxin to the tissue of the patient with a period of between about 3 months and about 4 months.

In some examples, periodically administering botulinum toxin to the tissue of the patient comprises periodically administering botulinum toxin to the tissue of the patient with a period of between about 8 weeks and about 24 weeks.

In some examples, periodically administering the neuropeptide of the CRF family to the tissue of the patient comprises periodically administering the neuropeptide of the CRF family to the tissue of the patient with a period of at least about 8 weeks.

In some examples, periodically administering the neuropeptide of the CRF family to the tissue of the patient comprises periodically administering the neuropeptide of the CRF family to the tissue of the patient with a period of less than about 8 weeks.

In some examples, periodically administering the neuropeptide of the CRF family to the tissue of the patient comprises periodically administering the neuropeptide of the CRF family to the tissue of the patient with a period of about 6 months.

In some examples, periodically administering the neuropeptide of the CRF family to the tissue of the patient comprises periodically administering the neuropeptide of the CRF family to the tissue of the patient with a period of about 3 months.

In some examples, periodically administering the neuropeptide of the CRF family to the tissue of the patient comprises periodically administering the neuropeptide of the CRF family to the tissue of the patient with a period of between about 3 months and about 6 months.

In some examples, periodically administering the neuropeptide of the CRF family to the tissue of the patient comprises periodically administering the neuropeptide of the CRF family to the tissue of the patient with a period of between about 3 months and about 4 months.

In some examples, periodically administering the neuropeptide of the CRF family to the tissue of the patient comprises periodically administering the neuropeptide of the CRF family to the tissue of the patient with a period of between about 8 weeks and about 24 weeks.

In some examples, periodically administering the neuropeptide of the CRF family to the tissue of the patient comprises periodically administering at least one of CRF, urocortin, urotensin-I, or sauvagine to the tissue of the patient.

In some examples, periodically administering the neuropeptide of the CRF family to the tissue of the patient comprises periodically administering CRF to the tissue of the patient.

In some examples, periodically administering botulinum toxin to the tissue of the patient includes periodically administering between about 5 Units and about 300 Units of botulinum toxin to the tissue of the patient.

In some examples, periodically administering the neuropeptide of the CRF family to the tissue of the patient includes periodically administering between about 75 µg and about 200 µg of the neuropeptide of the CRF family to the tissue of the patient.

In some examples, periodically administering the neuropeptide of the CRF family to the tissue of the patient includes periodically administering about 160 µg of the neuropeptide of the CRF family to the tissue of the patient.

In some examples, periodically administering the neuropeptide of the CRF family to the tissue of the patient includes periodically administering about 160 µg of the neuropeptide of the CRF family to the tissue of the patient, and periodically administering botulinum toxin to the tissue of the patient comprises administering about 5 Units of botulinum toxin to the tissue of the patient.

EXAMPLES

Example 1

Adult male New Zealand white rabbits were obtained from Bakkom Rabbitry (Viroqua, Wis.) and housed in the Association for Assessment and Accreditation of Laboratory Animal Care International (AAALAC)-approved animal facility at the University of Minnesota. All animal studies were approved by the Institutional Animal Care and Use Committee at the University of Minnesota, as well as complied with the guidelines for the Use of Animals in Research published by the Association for Research in Vision and Ophthalmology as well as the guidelines of the National Institutes of Health.

Rabbits were anesthetized using an intramuscular injection of ketamine:xylazine (1:1) at a dose of 10 mg/kg:2 mg/kg respectively. The cornea was anesthetized by placement of a drop of proparacaine HCl in the conjunctival cul-de-sac. Three groups of animals were prepared. Group One received a single injection of 5 Units of botulinum toxin A (available under the trademark BOTOX® (botulinum toxin), from Allergan, Inc., Irvine, Calif.) in 1 mL of sterile isotonic saline in one randomly selected upper eyelid. All injections were made by inserting the needle into the central region of the eyelid with the needle tip pointing toward the medial canthus, where half the volume is dispensed. The needle then was slowly pulled towards the needle entry point. With the needle in place, the syringe was rotated and the needle directed towards the lateral canthus. The same slow injection procedure was performed with slow withdrawal of the needle. After dispensing the full volume, the needle was left in place for 30 seconds to prevent leakage. This method reduced leakage, as only one needle stick was performed. Previous studies demonstrated that single injections of this volume spread into all regions of the treated eyelids. The rabbits in group one were examined 1, 2, or 4 weeks after botulinum toxin treatment. The contralateral upper eyelids were injected with only sterile saline in comparable volumes.

Group Two received a single injection of 5 Units of botulinum toxin according to the procedure described with respect to Group One. On post-treatment day 3 and post-treatment day 5, the botulinum toxin-affected upper eyelids of rabbits in Group Two were injected with CRF (available from Peninsula Labs., Belmont, Calif.) (150 µg CRF in 1 mL sterile saline). Eyelids of rabbits in Group Two were examined 2 weeks after the final CRF injection (two weeks after post-treatment day 5). The contralateral upper eyelids were injected with only sterile saline in comparable volumes.

Group Three received a single injection of 5 Units of botulinum toxin according to the procedure described with respect to Group One. On post-treatment day 3 and post-treatment day 5, the botulinum toxin-affected upper eyelids of rabbits in Group Three were injected with an anti-IGFIR (available from R and D Systems, Minneapolis, Minn.) at a dose of 30 µg anti-IGFIR per 1 mL sterile saline. Again eyelids of rabbits of Group Three were examined 2 weeks after the final anti-IGFIR injection. The contralateral upper eyelids were injected with only sterile saline in comparable volumes.

At the appropriate post-injection intervals, the rabbits were anesthetized deeply with ketamine and xylazine, followed by an overdose of barbiturate anesthesia. Both eyelids were trimmed to remove the fur and dissected completely to include the muscle at both the medial and lateral canthi. The eyelids were pinned to their in situ length in embedding molds, surrounded by tragacanth gum, frozen in methylbutane, chilled to a slurry on liquid nitrogen, and stored at –80° C. until sectioned and processed. The muscles of the eyelids were sectioned completely in the longitudinal plane at 12 µm, and the sections were mounted on gelatin-subbed microslides. Every $10^{th}$ section was immunostained for the presence of neuromuscular junctions using α-bungarotoxin conjugated to Alexa Fluor® 488 (available from Invitrogen Corp., Carlsbad, Calif.) at a concentration of 1 part antibody to 99 parts buffer overnight at 4° C. The slides were coverslipped with Vectashield® (available from Vector Labs., Burlingame, Calif.) mounting medium and analyzed the same day they were immunostained.

The muscle sections were examined for neuromuscular junction position and number using a Leica DMR microscope (available from Leica Microsystems Inc., Bannockburn, Ill.). Using the Topographer program of the Bioquant NovaPrime image analysis software (Bioquant Image Analysis Corp., Nashville, Tenn.), the area of the entire orbicularis oculi muscle in longitudinal section was measured at 1.6× magnification. Every neuromuscular junction was located at 20× magnification and marked with X and Y coordinates recorded in the Topographer program. This analysis was repeated for every $10^{th}$ section through substantially the entire eyelid. The Bioquant Topographer program was used to reconstruct the substantially the entire muscle, including the area outlines and locations of the neuromuscular junctions. This allowed for a three-dimensional reconstruction of substantially all of the neuromuscular junctions in their actual X, Y and Z planes within the muscle. Four orbicularis oculi muscles were examined for each of the control, Group One, Group Two, and Group Three Density of neuromuscular junctions was calculated as number of neuromuscular junctions per square millimeter ($mm^2$). Statistical significance was determined between the densities of neuromuscular junctions in the saline treated control muscles (orbicularis oculi), the eyelid muscles treated only with botulinum toxin, the muscles treated with botulinum toxin and CRF, and the muscles treated with botulinum toxin and anti-IGFIR. Statistical analysis was performed using an unpaired t-test aided by the Prism and StatMate software (available from GraphPad Software, Inc., La Jolla, Calif.). An F-test was used to verify that the variances of the different groups were not significantly different. Data were considered significantly different if $p<0.05$.

Figure 1B:
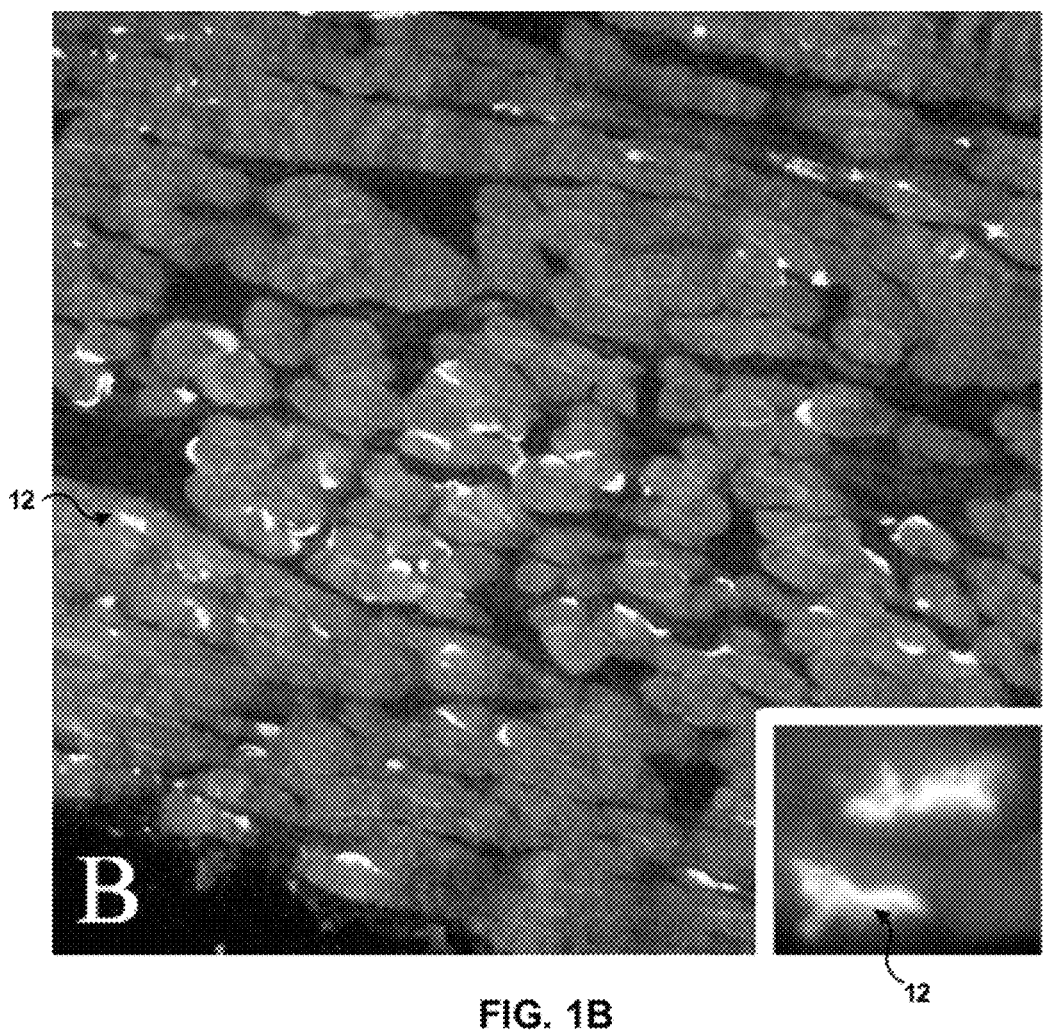
Figure 1C:
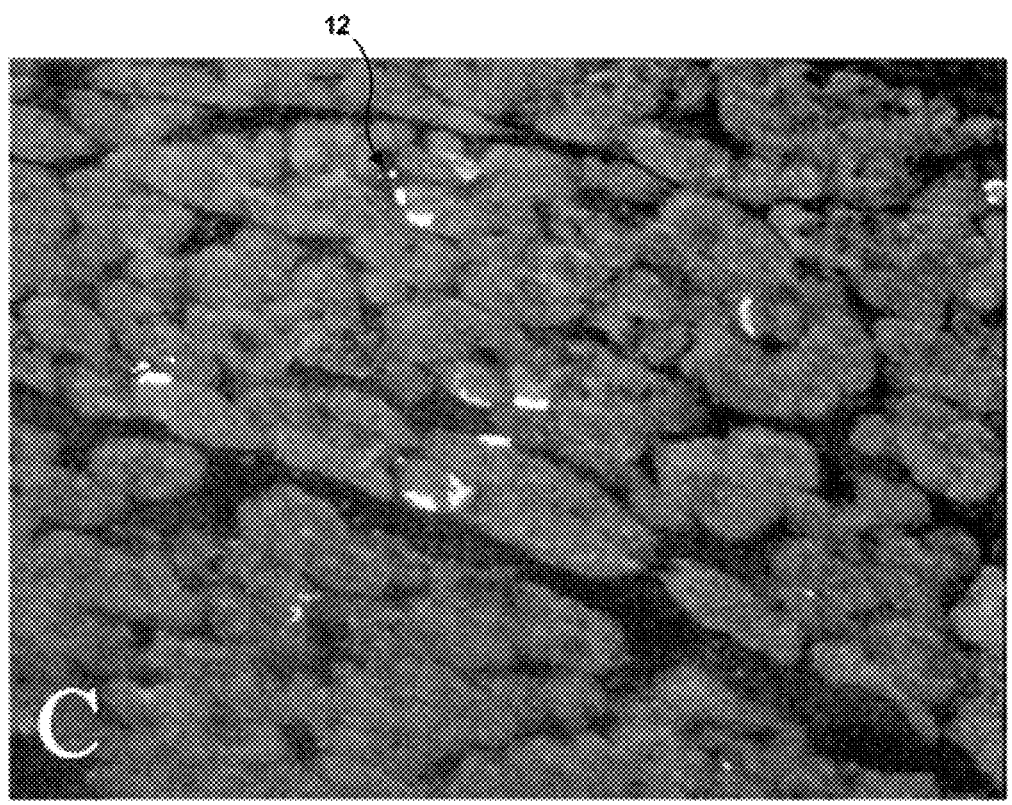
Figures 2A, 2B:
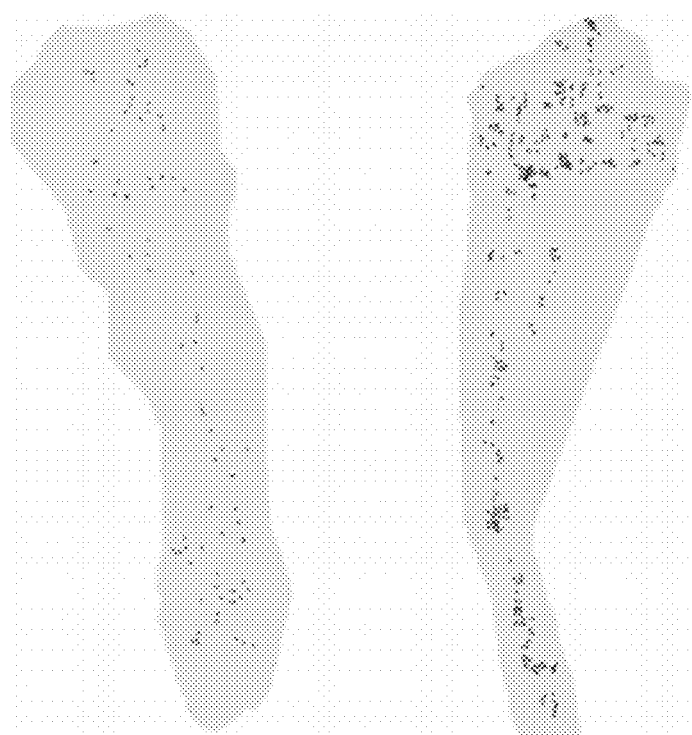
FIGS. 2A-2D are three-dimensional reconstructions of approximately 10% of the neuromuscular junctions in representative eyelid specimens.
Figures 2C, 2D:
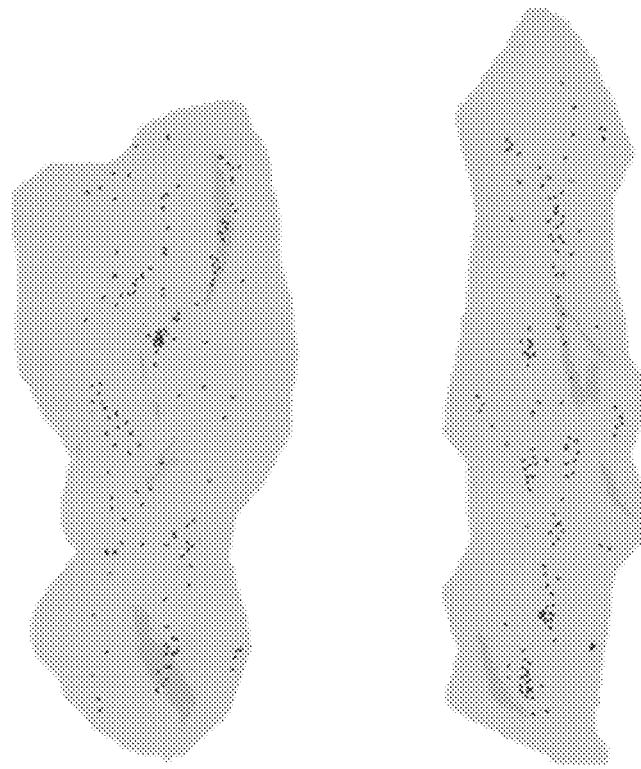
Figure 3:
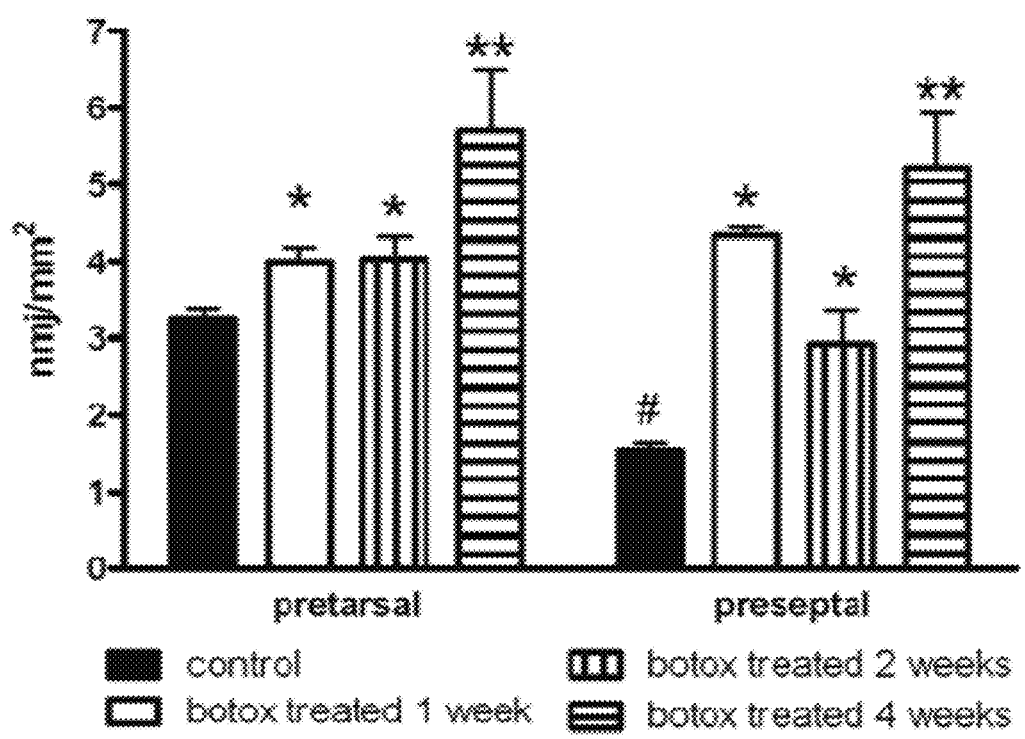
FIG. 3 is a bar diagram that illustrates quantification of neuromuscular junction density of various samples of orbicularis oculi muscles.
Figure 4:
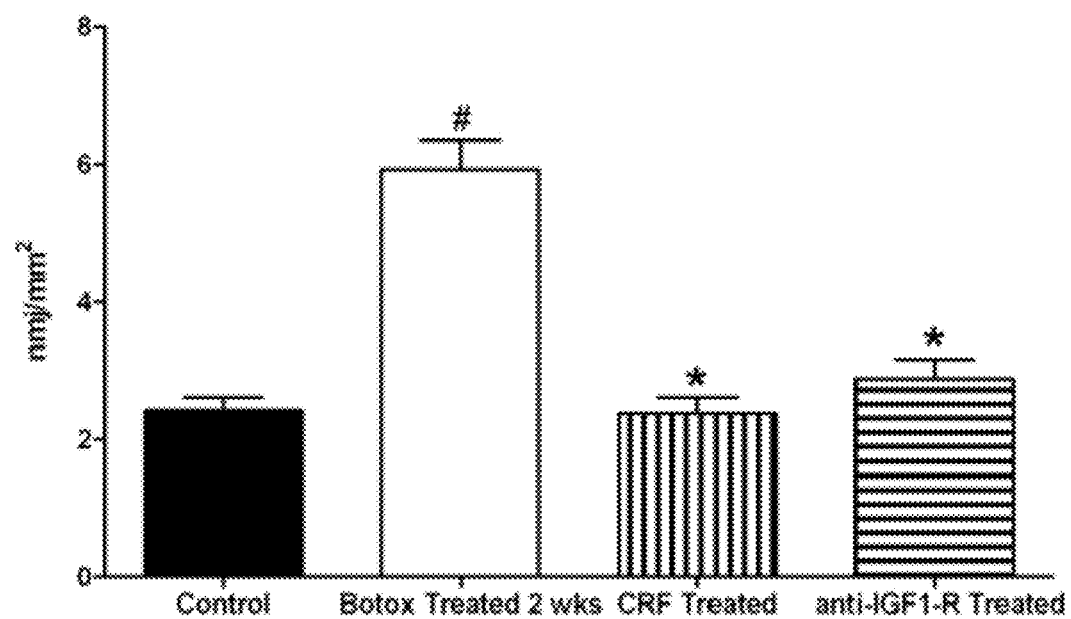
FIG. 4 is another bar diagram that illustrates quantification of neuromuscular junction density of various samples of orbicularis oculi muscles.
Figure 5:
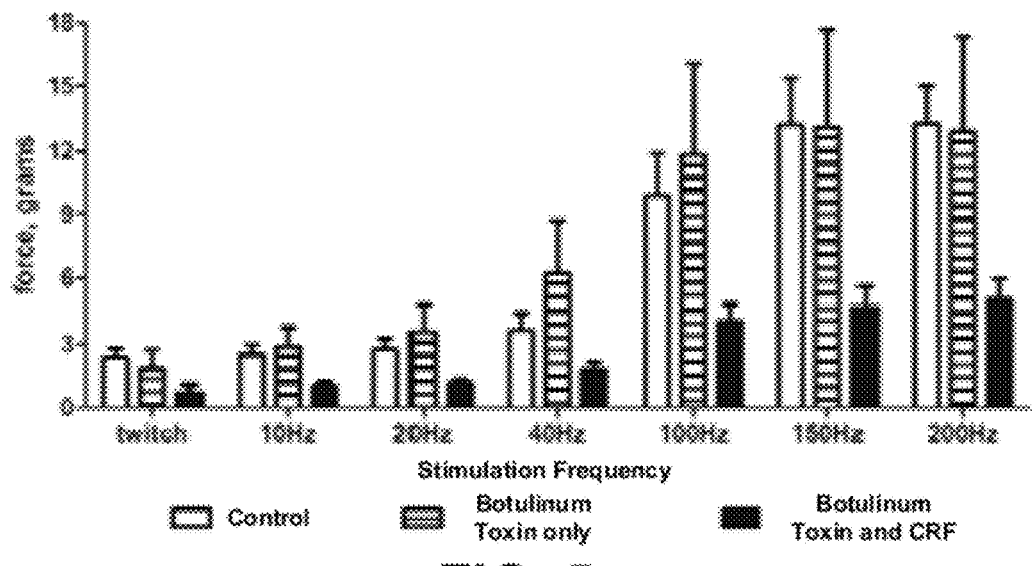
FIGS. 5 and 6 are bar graphs that show the averaged response of the superior rectus muscle to electrical stimulation at different frequencies.
Figure 6:
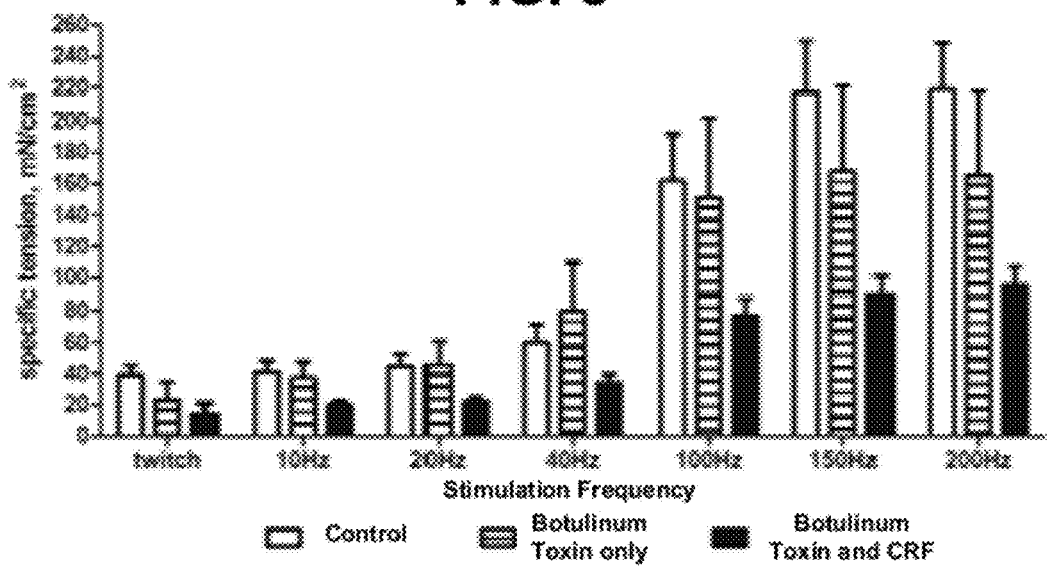
Figure 7:
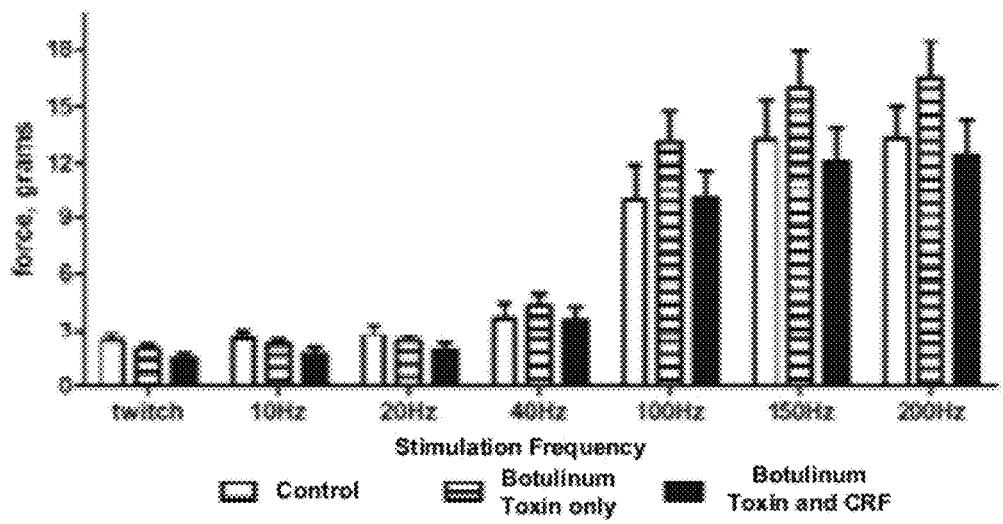
FIGS. 7 and 8 are bar graphs that show the averaged response of the superior rectus muscle to electrical stimulation at different frequencies
Figure 8:
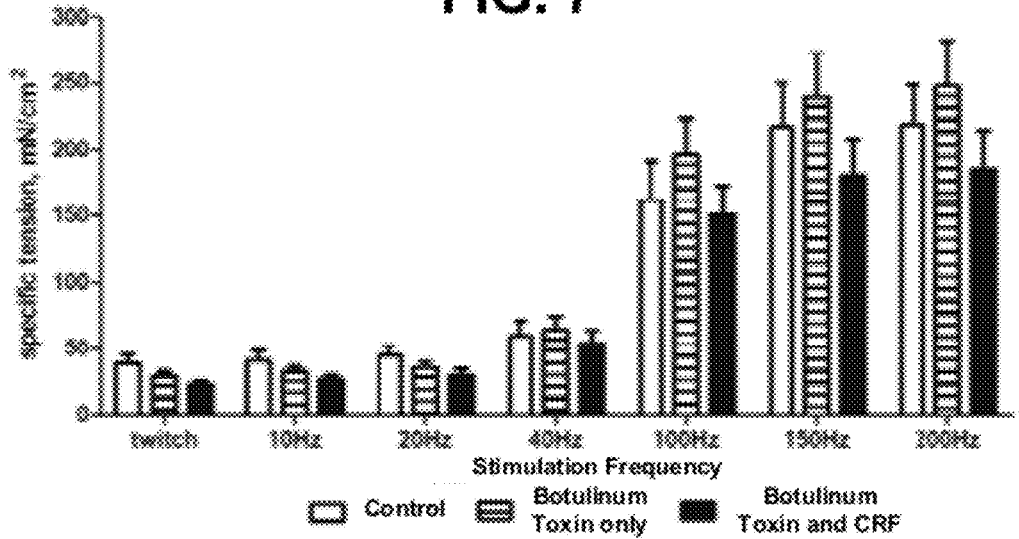

The effect of injection of botulinum toxin A on neuromuscular density in orbicularis oculi of adult rabbits was determined. The results are shown in FIGS. 1A-1C, 2A-2D, 3, and 4. FIGS. 1A-1C are photomicrographs of neuromuscular junctions stained with fluorescently labeled a-bungarotoxin. The neuromuscular junctions appear as bright areas 12 in FIGS. 1A-1C. FIGS. 2A-2D are three-dimensional reconstructions of approximately 10% of the neuromuscular junctions in representative eyelid specimens. FIG. 3 is a bar diagram that illustrates quantification of neuromuscular junction density of various samples of orbicularis oculi muscles. FIG. 4 is another bar diagram that illustrates quantification of neuromuscular junction density of various samples of orbicularis oculi muscles.

In the control samples (those injected with only saline), the neuromuscular junction density was 2-fold greater in the pretarsal region of normal (control) orbicularis oculi muscle compared to the preseptal region. The density of neuromuscular junctions was $3.30±0.14/mm^2$ and $1.55±0.09/mm^2$ in the pretarsal and preseptal regions, respectively. These results are shown in FIGS. 1A, 2A, 3 (the white bar), and 4 (the white bar).

In eyelids from Group One rabbits, the neuromuscular junction density increased significantly one week and two weeks after botulinum toxin A injection, particularly in the preseptal regions. In the pretarsal region, neuromuscular junction density was $4.0±0.21/mm^2$ after one and two weeks. In the preseptal region, neuromuscular junction densities were between about two and three times greater than control at 1 and 2 weeks post treatment, with densities of $4.4±01/mm^2$ and $2.9±0.4/mm^2$ respectively. The results after week one are shown in FIG. 3 as the vertical hatched bar. The results after week two are shown in FIGS. 1B, 2B, 3 (the black bar), and 4 (the black bar). At four weeks post-botulinum toxin treatment, the up-regulation of neuromuscular junctions in Group One was even greater when compared to control levels, and was also significantly greater than the neuromuscular junction density at 2 weeks. For Group One eyelids, densities in the pretarsal and preseptal regions at 4 weeks post-treatment were $5.7±0.8/mm^2$ and $5.23±0.7/mm^2$, respectively. The results at four weeks post-botulinum toxin treatment are illustrated as the gray bar in FIG. 3.

Injection of CRF into the botulinum toxin-treated eyelids resulted in neuromuscular junction densities that were not significantly different from the density in the control orbicularis oculi muscles, with the CRF-treated neuromuscular junction density at $2.39±0.23/mm^2$ compared to $2.42±0.19/mm^2$ in the control orbicularis oculi muscles. The results for the CRF and botulinum toxin-treated eyelids two weeks after injection of the botulinum toxin are shown in FIGS. 1C, 2C, and the gray bar of FIG. 4. As the combined total muscle neuromuscular junction density in the orbicularis oculi muscle increased almost 3-fold after the botulinum toxin A treatment to $5.9±0.43/mm^2$, it is notable that the up-regulation of neuromuscular junctions was substantially completely negated by the injection of CRF within days of the botulinum toxin.

Similarly, injection of anti-IGFIR within days of the botulinum toxin treatment resulted in substantially no increase in neuromuscular junction density compared to control levels, with neuromuscular junction density in the anti-IGFIR-treated orbicularis oculi muscles at $2.88±0.28/mm^2$ two weeks after botulinum toxin injection, compared to control levels at $2.4±0.19/mm^2$. The results for the anti-IGFIR and botulinum toxin-treated eyelids two weeks after injection of the botulinum toxin are shown in FIG. 2D and the hatched bar of FIG. 4.

Botulinum toxin A injection alone resulted in a significant increase in neuromuscular junction density, as previously demonstrated. Injection of the botulinum toxin-treated eyelids with either CRF or anti-IGFR substantially negated the botulinum toxin-induced de novo formation of neuromuscular junctions on the paralyzed muscles.

Local injection of either CRF or anti-IGFIR prevented the up-regulation of neuromuscular junctions that occurs after botulinum toxin A injection. This may increase the effective duration of a botulinum toxin A injection, which may decrease the life-time exposure of these patients to the toxin, with concomitant reduction in potential side-effects. Injection of anti-IGF is expected to function similarly to CRF and anti-IGFIR.

Example 2

Simultaneous injection of botulinum toxin A and CRF was also tested. Adult rabbit superior rectus muscle was injected with 5 units botulinum toxin A and 160 μg CRF in sterile isotonic saline in a single injection. The contralateral superior rectus muscle of each animal was injected with either an equivalent volume of saline or 5 units of botulinum toxin A in saline. After 2 weeks or 1 month, animals were euthanized and the superior rectus muscles removed. The superior rectus muscles were placed into oxygenated Krebs buffer and suspended from a lever arm and force transducer in in vitro incubation chambers. The muscles were stimulated by flanking platinum electrodes, and muscle force (grams) and specific tension ($mN/cm^2$) in response to stimulation at different stimulation frequencies were determined.

FIGS. 5 and 6 are bar graphs that show the averaged response of the superior rectus muscle to electrical stimulation at different frequencies two weeks after injection. Six superior rectus muscles were tested at each frequency. FIGS. 5 and 6 also include standard deviation bars. As shown in FIGS. 5 and 6, a significant reduction in force and in specific tension in the muscles that received the combined treatment (botulinum toxin A and CRF) was observed compared to samples injected with only saline and samples injected with 5 units of botulinum toxin A in saline. Note that at this dose of botulinum toxin A in rabbit superior rectus muscle, botulinum toxin A-treated muscles showed a variable response, with some showing force equal to the saline-treated control muscles.

FIGS. 7 and 8 are bar graphs that show the averaged response of the superior rectus muscle to electrical stimulation at different frequencies one month after injection. Six superior rectus muscles were tested at each frequency. FIGS. 7 and 8 also include standard deviation bars. A reduction in force generation with the combined treatment (compared to botulinum toxin A-only treatment or saline-only treatment) was also observed at one month after treatment, as shown in FIGS. 7 and 8.

Example 3

Adult male New Zealand white rabbits were obtained from Bakkom Rabbitry (Viroqua, Wis.) and housed in the Association for Assessment and Accreditation of Laboratory Animal Care International (AAALAC)-approved animal facility at the University of Minnesota. All animal studies were approved by the Institutional Animal Care and Use Committee at the University of Minnesota, as well as complied with the guidelines for the Use of Animals in Research published by the Association for Research in Vision and Ophthalmology as well as the guidelines of the National Institutes of Health.

Rabbits were anesthetized using an intramuscular injection of ketamine:xylazine (1:1) at a dose of 10 mg/kg:2 mg/kg respectively. The cornea was anesthetized by placement of a drop of proparacaine HCl in the conjunctival cul-de-sac. For each animal, one upper eyelid received a single injection of 5 Units of botulinum toxin (available under the trademark BOTOX® (botulinum toxin), from Allergan, Inc., Irvine, Calif.) and 160 μg CRF (available from Peninsula Labs., Belmont, Calif.) in sterile isotonic saline. The contralateral eyelid of each animal received a single injection of 5 Units of botulinum toxin A in 1 mL of sterile isotonic saline or a single injection of 1 mL of sterile isotonic saline (control).

All injections were made by inserting the needle into the central region of the eyelid with the needle tip pointing toward the medial canthus, where half the volume is dispensed. The needle then was slowly pulled towards the needle entry point. With the needle in place, the syringe was rotated and the needle directed towards the lateral canthus. The same slow injection procedure was performed with slow withdrawal of the needle. After dispensing the full volume, the needle was left in place for 30 seconds to prevent leakage. This method reduced leakage, as only one needle stick was performed. Previous studies demonstrated that single injections of this volume spread into all regions of the treated eyelids. The rabbits in group one were examined 1, 2, or 4 weeks after botulinum toxin treatment. The contralateral upper eyelids were injected with only sterile saline in comparable volumes.

At each of one week after injection, two weeks after injection, and one month after injection, some rabbits were anesthetized deeply with ketamine and xylazine, followed by an overdose of barbiturate anesthesia. Both eyelids were trimmed to remove the fur and dissected completely to include the muscle at both the medial and lateral canthi. The eyelids were pinned to their in situ length in embedding molds, surrounded by tragacanth gum, frozen in methylbutane, chilled to a slurry on liquid nitrogen, and stored at −80° C. until sectioned and processed. The muscles of the eyelids were sectioned completely in the longitudinal plane at 12 μm, and the sections were mounted on gelatin-subbed microslides. Every $10^{th}$ section was immunostained for the presence of neuromuscular junctions using α-bungarotoxin conjugated to Alexa Fluor® 488 (available from Invitrogen Corp., Carlsbad, Calif.) at a concentration of 1 part antibody to 99 parts buffer overnight at 4° C. The slides were coverslipped with Vectashield® (available from Vector Labs., Burlingame, Calif.) mounting medium and analyzed the same day they were immunostained.

The muscle sections were examined for neuromuscular junction position and number using a Leica DMR microscope (available from Leica Microsystems Inc., Bannockburn, Ill.). Using the Topographer program of the Bioquant NovaPrime image analysis software (Bioquant Image Analysis Corp., Nashville, Tenn.), the area of the entire orbicularis oculi muscle in longitudinal section was measured at 1.6× magnification. Every neuromuscular junction was located at 20× magnification and marked with X and Y coordinates recorded in the Topographer program. This analysis was repeated for every $10^{th}$ section through substantially the entire eyelid. The Bioquant Topographer program was used to reconstruct the substantially the entire muscle, including the area outlines and locations of the neuromuscular junctions. This allowed for a three-dimensional reconstruction of substantially all of the neuromuscular junctions in their actual X, Y and Z planes within the muscle. Four orbicularis oculi muscles were examined for each of the control, Group One, Group Two, and Group Three Density of neuromuscular junctions was calculated as number of neuromuscular junctions per square millimeter (mm$^2$). Statistical significance was determined between the densities of neuromuscular junctions in the saline treated control muscles (orbicularis oculi), the eyelid muscles treated only with botulinum toxin, and the muscles treated with botulinum toxin and CRF. Statistical analysis was performed using an unpaired t-test aided by the Prism and StatMate software (available from GraphPad Software, Inc., La Jolla, Calif.). An F-test was used to verify that the variances of the different groups were not significantly different. Data were considered significantly different if p≤0.05.

Figure 9:
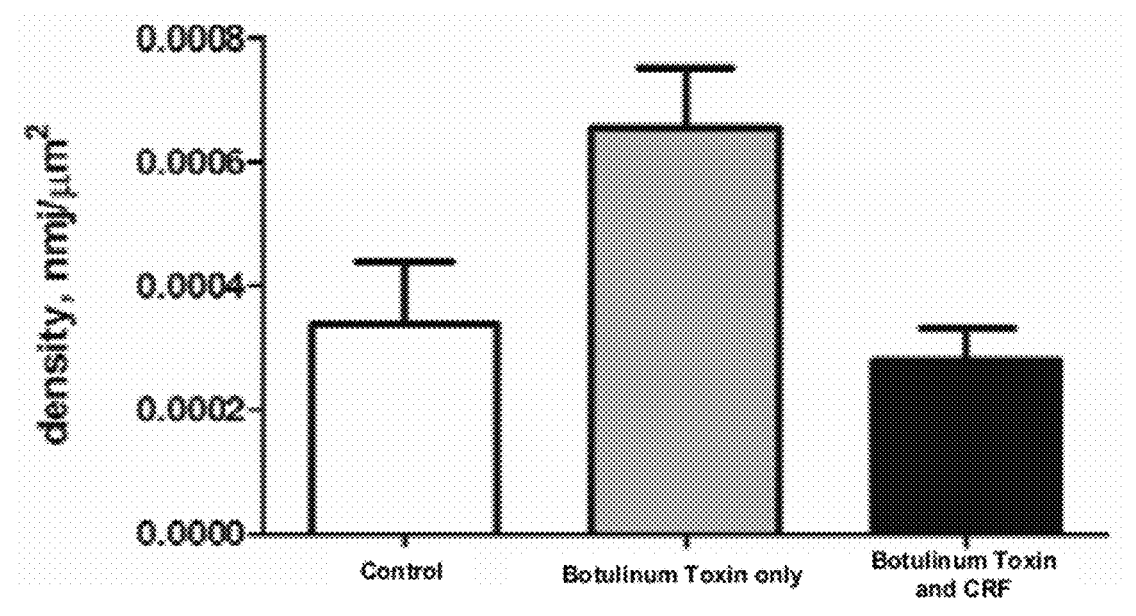

FIG. 9 is a bar graph that shows results at two weeks post-injection. Injection with Botulinum Toxin A alone results in a significant increase in neuromuscular junction density compared to the control. After a single injection of botulinum toxin A and CRF, sprouting of paralyzed nerves that would normally occur in the absence of CRF is prevented. The density of neuromuscular junctions (nmj) in the samples injected with botulinum toxin A and CRF is substantially the same as in the saline injected control eyelids.

Various examples have been described. These and other examples are within the scope of the following claims.

The invention claimed is:

1. A method comprising:
   administering an amount of botulinum toxin to a facial muscle tissue of a patient so as to cause paresis or paralysis of said muscle tissue; and
   administering an amount of a neuropeptide of the corticotropin releasing factor (CRF) family to said muscle tissue of the patient effective to increase the duration of said paresis or paralyis.

2. The method of claim 1, wherein administering the neuropeptide of the CRF family to the tissue of the patient comprises administering a neuropeptide selected from the group consisting of CRF, urocortin, urotensin-I, sauvagine, and combinations thereof to the tissue of the patient.

3. The method of claim 2, wherein administering the neuropeptide selected from the group consisting of CRF, urocortin, urotensin-I, sauvagine, and combinations thereof to the tissue of the patient comprises administering CRF to the tissue of the patient.

4. The method of claim 3, wherein the botulinum toxin is type A and/or type B.

5. The method of claim 2, wherein administering the neuropeptide of the CRF family to the tissue of the patient comprises administering the neuropeptide of the CRF family to the tissue of the patient at the same time as administering the botulinum toxin to a tissue of a patient.

6. The method of claim 5, wherein administering the botulinum toxin to the tissue of the patient and administering the neuropeptide of the CRF family to the tissue of the patient comprise injecting a solution including the botulinum toxin and the neuropeptide or the CRF family into the tissue of the patient.

7. The method of claim 2, wherein administering the botulinum toxin to the tissue of the patient comprises administering the botulinum toxin to the tissue of the patient at a first time, and wherein administering the neuropeptide of the CRF family to the tissue of the patient comprises administering the neuropeptide of the CRF family to the tissue of the patient at a second time different than the first time.

8. The method of claim 2, wherein administering the neuropeptide of the CRF family to the tissue of the patient comprises injecting a solution including the neuropeptide of the CRF family into the tissue of the patient and/or wherein administering the botulinum toxin to the tissue of the patient comprises injecting a solution including the botulinum toxin into the tissue of the patient.

9. The method of claim 2, wherein administering botulinum toxin to the tissue of the patient comprises administering botulinum toxin to the tissue of the patient a first time, wherein the method further comprises administering botulintun toxin to the tissue of the patient a second time.

10. The method of claim 9, wherein a time between administering botulinum toxin to the tissue of the patient the first time and administering botulinum toxin to the tissue of the patient the second time is greater than about 8 weeks.

11. The method of claim 9, wherein a time between administering botulinum toxin to the tissue of the patient the first time and administering botulinum toxin to the tissue of the patient the second time is between about 3 months and about 6 months.

12. The method of claim 2, wherein administering the neuropeptide of the CRF family to the tissue of the patient comprises administering the neuropeptide of the CRF family to the tissue of the patient a first time, wherein the method further comprises administering the neuropeptide of the CRF family to the tissue of the patient a second time.

13. The method of claim 12, wherein a time between administering the neuropeptide of the CRF family to the tissue of the patient the first time and administering the neuropeptide of the CRF family to the tissue of the patient the second time greater than about 8 weeks.

14. The method of claim 12, wherein a time between administering the neuropeptide of the CRF family to the tissue of the patient the first time and administering the neuropeptide of the CRF family to the tissue of the patient the second time is between about 3 months and about 6 months.

15. The method of claim 2, wherein administering the botulinum toxin to the tissue of the patient comprises periodically administering the botulinum toxin to the tissue of the patient, and wherein administering the neuropeptide of the CRF to the tissue of the patient comprises periodically administering the neuropeptide of the CRF family to the tissue of the patient.

16. The method of claim 15, wherein periodically administering botulinum toxin to the tissue of the patient comprises periodically administering botulinum toxin to the tissue of the patient according to a first schedule, and wherein periodically administering the neuropeptide of the CRF family to the tissue of the patient comprises periodically administering the neuropeptide of the CRF family to the tissue of the patient according to a second schedule.

17. The method of claim 16, wherein the first schedule is the same as the second schedule.

18. The method of claim 16, wherein the first schedule is different than the second schedule.

19. The method of claim 15, wherein periodically administering botulinum toxin to the tissue of the patient comprises periodically administering botulinum toxin to the tissue of the patient with a period of at least about 8 weeks.

20. The method of claim 15, wherein periodically administering botulinum toxin to the tissue of the patient comprises periodically administering botulinum toxin to the tissue of the patient with a period of between about 3 months and about 6 months.

21. The method of claim 15, wherein periodically administering the neuropeptide of the CRF family to the tissue of the patient comprises periodically administering the neuropeptide of the CRF family to the tissue of the patient with a period of at least about 8 weeks.

22. The method of claim 15, wherein periodically administering the neuropeptide of the CRF family to the tissue of the patient comprises periodically administering the neuropeptide of the CRF family to the tissue of the patient with a period of between about 3 months and about 6 months.

23. The method of claim 2, wherein administering botulinum toxin to the tissue of the patient comprises administering between about 2.5 Units and about 150 Units of botulinum toxin A to the tissue of the patient or administering between about 50 Units and about 3750 Units of botulinum toxin B to the tissue of the patient.

24. The method of claim 23, wherein administering the botulinum toxin to the tissue of the patient comprises administering about 5 Units of botulinum toxin A to the tissue of the patient.

25. The method of claim 2, wherein administering the neuropeptide of the CRF family to the tissue of the patient comprises administering between about 75 µg and about 200 µg of the neuropeptide of the CRF family to the tissue of the patient.

26. The method of claim 25, wherein administering the neuropeptide of the CRF family to the tissue of the patient comprises administering about 160 µg of the neuropeptide of the CRF family to the tissue of the patient.

\* \* \* \* \*

UNITED STATES PATENT AND TRADEMARK OFFICE
CERTIFICATE OF CORRECTION

PATENT NO. : 8,791,072 B2  Page 1 of 1
APPLICATION NO. : 13/406289
DATED : July 29, 2014
INVENTOR(S) : Lee et al.

It is certified that error appears in the above-identified patent and that said Letters Patent is hereby corrected as shown below:

In the Claims

Column 19, line 33, Claim 1, delete "paralyis" and insert --paralysis--, therefor Column 19, line 55, Claim 6, delete "or" and insert --of--, therefor Column 20, line 7, Claim 9, delete "botulintun" and insert --botulinum--, therefor Column 20, line 29, Claim 13, after "time", insert --is--, therefor Column 20, line 39, Claim 15, after "CRF", insert --family--, therefor Signed and Sealed this
Twenty-first Day of October, 2014

Michelle K. Lee
*Deputy Director of the United States Patent and Trademark Office*